United States Patent [19]

Kalopissis et al.

[11] 4,228,259

[45] Oct. 14, 1980

[54] WATER-SOLUBLE CATIONIC POLYMER DYE COMPOUNDS AND PROCESS FOR PRODUCING THE SAME

[75] Inventors: Gregoire Kalopissis, Neuilly; Alexandre Zysmann; Henri Sebag, both of Paris; Guy Vanlerberghe, Commune de Villenaude; Jean-Louis Huron, Mulhouse; Andree Bugaut, Boulogne, all of France

[73] Assignee: L'Oreal, Paris, France

[21] Appl. No.: 822,912

[22] Filed: Aug. 8, 1977

[30] Foreign Application Priority Data

Aug. 12, 1976 [FR] France ............................ 76 24618

[51] Int. Cl.$^2$ ............................................. C08G 69/48
[52] U.S. Cl. .................................... 525/435; 260/9; 260/158; 260/377; 260/396 R; 260/396 N; 260/558 R; 8/405; 525/417; 521/184; 528/336; 528/342; 528/424
[58] Field of Search .................. 528/424, 342, 310; 525/435

[56] References Cited

U.S. PATENT DOCUMENTS

| | | | |
|---|---|---|---|
| 2,396,275 | 3/1946 | Kirby | 260/78 SC |
| 2,423,460 | 7/1947 | McQueen | 260/78 SC |
| 2,428,108 | 9/1947 | McQueen | 260/78 SC |
| 2,463,838 | 3/1949 | Wilson | 260/78 SC |
| 2,994,693 | 8/1961 | Blake et al. | 260/78 R |
| 3,081,281 | 3/1963 | Beghin | 260/78 R |
| 3,147,235 | 9/1964 | Zweidler et al. | 260/78 R |
| 3,251,743 | 5/1966 | Hahn et al. | 260/29.6 H |
| 3,278,486 | 11/1966 | Meek et al. | 260/78 R |
| 3,403,200 | 9/1968 | Randall | 260/78 R |
| 3,535,255 | 10/1970 | Kalopissis et al. | 260/42.21 |
| 3,617,165 | 11/1971 | Kalopissis et al. | 8/10.1 |
| 3,720,653 | 3/1973 | Kalopissis et al. | 526/264 |
| 3,743,622 | 7/1973 | Wagner et al. | 8/10.1 |
| 3,790,512 | 2/1974 | Wagner et al. | 8/10.1 |
| 3,915,635 | 10/1975 | Kalopissis et al. | 8/10.1 |
| 3,919,265 | 11/1975 | Bugaut et al. | 260/396 R |
| 4,013,787 | 3/1977 | Varierberghe et al. | 424/70 |

FOREIGN PATENT DOCUMENTS 1167161 10/1969 United Kingdom .

OTHER PUBLICATIONS

Chem. Abstracts, vol. 61 (1964), 1343h, Bykov et al.
Chem. Abstracts, vol. 69 (1968), 20071b, Krasovitskii et al.
Chem. Abstracts, vol. 8 (1974), 49064q, Gangneux.
Chem. Abstracts, vol. 85 (1976), 178021a, Fatten et al.

*Primary Examiner*—Harold D. Anderson
*Attorney, Agent, or Firm*—Cushman, Darby & Cushman

[57] ABSTRACT

A dye for keratinic material comprises a water-soluble cationic polymer having a molecular weight ranging between about 800 and 10,000 and having secondary, tertiary or quaternary ammonium amine groups wherein said amine groups are either a part of, or aid in the direct or indirect linking to the polymer chain, an aryl or arylaliphatic chromophore or chromogen group carrying compound, with the proviso that when the main chain of the polymer has amine groups derived from the said chromophore or chromogen group carrying compound, the said main chain must also have at least 10 percent aliphatic amine groups relative to the total number of amine groups of the said chain.

5 Claims, No Drawings

WATER-SOLUBLE CATIONIC POLYMER DYE COMPOUNDS AND PROCESS FOR PRODUCING THE SAME

It is known that keratinic fibers are customarily dyed with coloring agents which tend to penetrate the hair. This technique presumes that the dyes used are soluble in the carrier employed and that they have a certain affinity for keratinic fiber. However, these two conditions considerably reduce the number of compounds that can be used for dyeing keratinic fiber. It has also been noted that when some known compounds are used for dyeing hair, they not only have an affinity for keratinic fiber, but also an affinity for the skin, so that dyeing the hair results in a coloration of the scalp and hands of the person applying the dye, which is a disadvantage of this technique.

Heretofore, proposals have been made to use colored polymers for dyeing keratinic fibers, which polymers formed a sheath around the fiber. See, for example, U.S. Pat. Nos. 3,619,101, 3,617,165, 3,567,678, 3,797,994, 3,720,653, 3,535,255, 3,597,468, 3,763,086 and 3,915,635. However, these colored polymers, which are derived from polymers of average or high molecular weight and are only soluble in solvents such as alcohol or a water-alcohol mixture are employed as dye lacquers. These polymers have two disadvantages: first, they are not water-soluble and secondly, they can be eliminated by brushing the keratinic fibers or by shampooing. Thus the coloration of the fibers cannot be considered to be lasting.

The present invention, on the other hand, relates to a new dye which is useful in coloring keratinic fibers, this dye comprising at least one polymer which has a strong affinity for the keratinic fiber to be treated because it contains an aliphatic amine group which facilitates the adsorption of the polymer on said fiber. This polymer is water-soluble and contains a chromophore group which imparts coloration to the polymer. The polymer, which remains outside the keratinic fiber, makes it possible to use a large number of direct dyes for coloring the fibers, these direct dyes not, in themselves, being water-soluble or having any affinity for the keratinic fiber. The new dye according to the present invention has a high degree of resistance to washing with water or detergent compositions and it also resists abrasion very well. Therefore, the dye of the present invention can be used in dye compositions to obtain long-lasting coloring, since the coloring is resistant to shampooing and brushing. However, it is possible to clean the keratinic fibers treated with the polymer substance of the present invention by means of an oxidizing agent, such as a persulphate or $H_2O_2$, or by means of a solvent. Another advantage of the new dye of the present invention is the avoidance of any toxicity problems related to the use of dyes or dye precursors incorporated into the polymer, since the chromophore or chromogen group carriers are not in a free state and are part of the polymer which remains outside the hair and which, because of its molecular weight, cannot diffuse through the skin. This advantage of the dye according to the present invention is of particular importance in the dyeing of living human hair.

The term "chromophore or chromogen group carrying compound" (CGCC) will be used herein to designate compounds with groups that impart color to them or compounds with groups which, by means of an appropriate transformation, can subsequently impart color to them.

Thus, one object of the present invention is a new dye comprising a water-soluble cationic polymer, having a molecular weight of between approximately 800 and 10,000, and having secondary, tertiary or quaternary ammonium amine groups which either are part of, or aid in the direct or indirect linking to the polymer chain of, an aryl or aryl-aliphatic CGCC, it being understood that if the main chain has amine groups derived from the CGCC, the main chain must also have at least 10% aliphatic amine groups relative to the total number of amine groups of the chain.

It has been noted that according to the present invention, the affinity of certain water-soluble cation resins for keratinic fibers can be used to advantage in obtaining the resistance of the dyes to rinsing and washing as well as a certain number of other advantages described below. Cationic polycondensates that can be employed as hair conditioners have already been described, particularly in U.S. Pat. Nos. 3,917,817 and 4,013,787; U.S. patent applications Ser. Nos. 528,577 and 577,836; U.S. patent application Ser. Nos. 742,116 and 742,118. The polycondensates of these U.S. patents and patent applications are described briefly below:

U.S. Pat. No. 3,917,817

The cationic polymer of the present invention is characterized by the fact that the cationic groups are part of the main polymer chain and that they are essentially derived from bisecondary heterocyclic amines, preferably, piperazine. Structurally, the low molecular weight, film-forming, cationic polymer of the present invention can be represented by the pattern $$-A-Z-A-Z-A-Z- \qquad (I)$$

wherein

A represents a radical derived from a heterocycle containing two secondary amine functions and, preferably, the radical

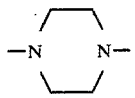

and

Z represents the symbol P or B', each of which independently represents a vivalent radical selected from the group consisting of (i) hydroxypropylene, (ii) alkylene having up to 5 carbon atoms inclusive and interrupted by 1-2 members selected from the group consisting of —CONH and

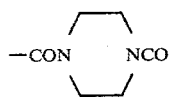

and (iii) hydroxy alkylene wherein the alkylene moiety has up to 6 carbon atoms inclusive and is interrupted by a member selected from the group consisting of alkylamine wherein the alkyl moiety has 12 to 16 carbon atoms, benzylamine, oleylamine and oxygen.

Often, polymers of the present invention are those in which A has the meaning given above and B and B' each independently represent a branched or straight chain radical selected from the group consisting of hydroxyalkylene having 1–6 and, preferably, 3 carbon atoms, lower alkyl-carbonamide-lower alkyl-carbonamide-lower alkyl having 5 to 8 and, preferably 6 to 7 carbon atoms, hydroxypropyl-oxyhydroxypropyl, hydroxypropyl-alkylaminohydroxypropyl wherein the alkyl moiety has 12 to 16 carbon atoms, hydroxypropyl-alkenylaminohydroxypropyl wherein the alkenyl moiety has 18 carbon atoms, hydroxypropylpiperazinyl-hydroxypropyl, propionyl-piperazinylpropionyl and hydroxypropyl-benzylamino-hydroxypropyl.

The polymers of the present invention are more generally strictly alternated, i.e., of the type

    (II)

wherein A and B have the meanings given above.

These rigorously alternated polymers, which can be used in the present invention, can be prepared by conventional processes such as by polyaddition or polycondensation of (a) piperazine or a derivative thereof such as, for example, N,N'bis(hydroxyethyl)piperazine, or (b) a bifunctional compound.

U.S. Pat. No. 4,013,787

The cationic polymer of this first embodiment of the present invention is characterized by the fact that the cationic groups are part of the main polymer chain and that they are essentially derived from bisecondary heterocyclic amines, preferably, piperazine. Structurally, the low molecular weight, film-forming, cationic polymer of the first embodiment can be represented by the pattern

    (I)

wherein

A represents a radical derived from a heterocycle containing two secondary amine functions and, preferably, the radical

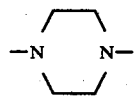

and

Z represents the symbol B or B', each of which independently represents a bivalent radical selected from the group consisting of (i) hydroxypropylene, (ii) alkylene having up to 5 carbon atoms inclusive and interrupted by 1–2 members selected from the group consisting of —CONH,

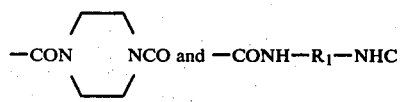

wherein R₁ represents an alkylene radical having up to 6 carbon atoms, preferably isopropylidene, and (iii) hydroxy alkylene wherein the alkylene moiety has up to 6 carbon atoms inclusive and is interrupted by a member selected from the group consisting of alkylamine wherein the alkyl moiety has 8 to 18 carbon atoms, benzylamine, oleylamine and oxygen.

Further, the cationic polymers of the present invention can also, in certain cases, be of the pattern

    (III)

i.e., be made up of polymer chains in which A, representing a bisecondary heterocyclic amine group, for example, the piperazine group is distributed regularly, the two B and B' groups designated by Z in formula (I) being distributed statistically. This type of polymer is obtained when piperazine or one of its derivatives is condensed with a mixture of two bifunctional derivatives.

Ser. No. 528,577

A cosmetic composition for the hair comprises at least one water-soluble crosslinked polymer selected from the group consisting of (1) crosslinked polymer obtained by crosslinking a polyamino-polyamide with a crosslinking agent, said polyamino-polyamide being prepared by the polycondensation of (a) an acidic compound selected from the group consisting of (i) organic dicarboxylic acid, (ii) ethylenically unsaturated aliphatic mono- or di-carboxylic acid, (iii) ester of said acids of (i) and (ii), and (iv) mixtures of (i), (ii) and (iii) on (b) a polyamine selected from the group consisting of bis primary and mono- or bis-secondary polyalkylene polyamines, said polyamine (b) being replaceable by a member selected from the group consisting of (1) 0–20 mole percent hexamethylene diamine, (2) 0–40 mole percent bis-primary amine and (3) 0–40 mole percent bis-secondary amine, said crosslinking agent being selected from the group consisting of epihalohydrins, diepoxides, dianhydrides and bis unsaturated derivatives, and being employed in amounts of 0.025–0.35 mole per amine group in said polyamino-polyamide and (2) the crosslinked polymer of (1) alkylated with an alkylating agent selected from the group consisting of (a) epoxides, (b) ethylenically unsaturated compounds, (c) chloroacetic acid, and (d) alkane sultone selected from the group consisting of propane sultone and butane sultone. The said crosslinked polymer is soluble in water in amounts of 10 weight percent thereof without essentially any gel formation and a 10 weight percent aqueous solution of the said crosslinked polymer has a viscosity greater than 3 centipoises at 25° C.

Ser. No. 577,836

A quaternized polymer for use as a cosmetic agent, has recurring units of the formula

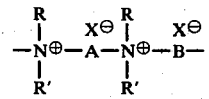

wherein

R is lower alkyl or —CH₂—CH₂OH;

R' is an aliphatic, alicyclic or arylaliphatic radical containing a maximum of 20 carbon atoms, or R and R' together with the nitrogen atom to which they are attached form a heterocycle capable of containing a heteroatom other than nitrogen;

A is a divalent group selected from (1) o-, m- or p- xylylidene of the formula

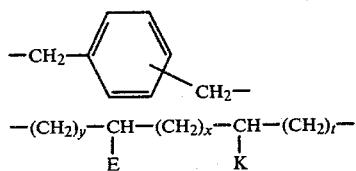

$$-(CH_2)_y-\underset{E}{CH}-(CH_2)_x-\underset{K}{CH}-(CH_2)_t- \quad (2)$$

wherein x, y and t are whole numbers ranging from 0 to 11 such that the sum (x+y+t) is greater than or equal to 0 and lower than 18, and E and K represent hydrogen or an aliphatic radical having less than 18 carbon atoms, (3) $-(CH_2)_n-S-(CH_2)_n-$,
(4) $-(CH_2)_n-O-(CH_2)_n-$,
(5) $-(CH_2)_n-S-S-(CH_2)_n-$,
(6) $-(CH_2)_n-SO-(CH_2)_n-$,
(7) $-(CH_2)_n-SO_2-(CH_2)_n-$ and (8)

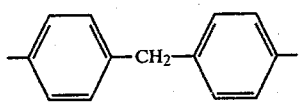

wherein n is equal to 2 or 3;
B represents a divalent group selected from
(1) o-, m- or p- xylylidene of the formula

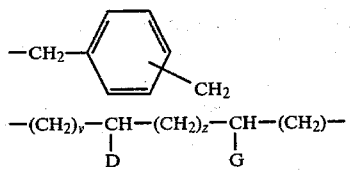

$$-(CH_2)_v-\underset{D}{CH}-(CH_2)_z-\underset{G}{CH}-(CH_2)_u- \quad (2)$$

wherein D and G represent hydrogen or an aliphatic radical having less than 18 carbon atoms and v, z and u are whole numbers ranging from 0 to 11, with two of v, z and u simultaneously being capable of being 0, such that the sum (v+z+u) is greater than or equal to 1 and lower than 18 and such that the sum (v+z+u) is greater than 1 when the sum (x+y+t) is equal to 0, $$-CH_2-\underset{\underset{OH}{|}}{CH}-CH_2- \text{ and} \quad (3)$$

$$-(CH_2)_n-O-(CH_2)_n- \quad (4)$$

wherein n is 2 or 3; and
$X^\ominus$ is an anion derived from an organic or mineral acid. The quaternized polymer is employed in cosmetic compositions for the hair and skin.

Ser. No. 742,116

Crosslinked aminated polymers having quaternized ammonium groups are employed in cosmetic compositions for application to the hair or skin. The polymer has recurring units of the formula

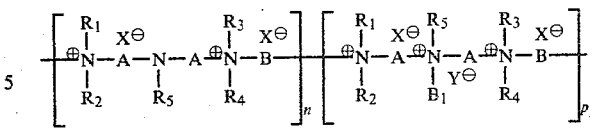

wherein A is polymethylene having 2–3 carbon atoms; $B_1$ and B are polymethylene having 3–10 carbon atoms, xylylidenyl group $-CH_2-C_6H_4-CH_2-$ (ortho, meta or para), $(CH_2)_x-O-(CH_2)_x$ wherein x is 2 or 3 or $-CH_2-CHOH-CH_2-$; $R_1$ and $R_3$ represent an aliphatic radical having 1–12 carbon atoms; $R_2$ and $R_4$ represents an aliphatic radical having 1–20 carbon atoms; $R_5$ is hydrogen or an aliphatic, alicyclic, aryl or arylaliphatic radical containing 1–20 carbon atoms; X is a halide anion; Y is a halide anion; and n and p are whole numbers.

Ser. No. 742,118

Quaternized polyamine polymers are employed in cosmetic compositions for application to the hair or skin. The polymer has recurring units of the formula:

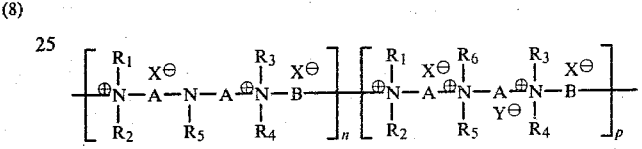

wherein A is polymethylene having 2–10 carbon atoms; B is selected from polymethylene having 3–10 carbon atoms, xylylidenyl group $-CH_2-C_6H_4-CH_2-$ ortho, meta or para, $-(CH_2)_x-O-(CH_2)_x-$ wherein x is 2 or 3; or $-CH_2-CHOH-CH_2$; $R_1$ and $R_3$ represent an aliphatic radical having 1–12 carbon atoms; $R_2$ and $R_4$ represent an aliphatic radical having 1–20 carbon atoms; $R_5$ is hydrogen or an aliphatic, alicyclic, aryl or arylaliphatic radical containing 1–20 carbon atoms; $R_6$ is an aliphatic or arylaliphatic radical containing 1–20 carbon atoms; X is a halide anion; Y is selected from a halide anion, $SO_4H^\ominus$ or $CH_3SO_4^\ominus$; and n and p are whole numbers with p being able to be 0, such that the ratio p/n+p ranges from 0 to 0.95.

These cationic polycondensates have a great affinity for hair, an affinity which increases as the hair becomes sensitized by bleaching or permanent waving. It has been noted that if colored compounds of color precursors are grafted onto these cation resins or if these compounds are introduced into the skeleton of said resins, their great affinity for keratinic fiber is still maintained; it being understood that if the main chain has amine groups which are part of the CGCC, it must also have at least 10% aliphatic amine groups relative to the total number of amine groups of the chain. These aliphatic amine groups make it possible for the polymer to be adsorbed onto the keratinic fiber. Indeed, the keratinic fiber is a negatively charged anion base which cooperates with the cation sites corresponding to the aliphatic amine groups of the polymer according to the present invention.

If the cation polymers of the present invention are derived from cation polymers previously employed as conditioners for the hair, one embodiment of the present invention comprises grafting a colored product, coloring agent or coloring agent precursor onto some of the amine groups of the cationic polymer. However, to maintain the polymer's keratinic fiber adsorption properties, the amine sites must not all be replaced by the CGCC results so that the polymer's affinity for keratinic fiber is not eliminated. The CGCC grafted onto the polymer may or may not be water-soluble, since the solubility of the colored cation polymer according to the invention depends on the solubility of the corresponding polymer being grafted with the CGCC residue. In one variant, the polymer of the invention is linear or branched, but not reticulated; in another variant, the polymer may be slightly reticulated, but if it is, the reticulation is limited so that there will be no excessive decrease in the water-solubility of the polymer. The polymers according to the present invention are water soluble. They can be used not only in an aqueous solution, but in a water-solvent medium as well; the solubility subsisting when solvents such as ethanol, alkylene glycols, glycol ethers or similar products are added.

The colored polymers according to the present invention can be obtained by the three processes described below.

In a first process, the dyes according to the present invention can be obtained by reacting reactive colored compounds with cation resins having primary, secondary or tertiary alkylatable amine groups.

In a second process, the dyes according to the present invention can be obtained by reacting colored compounds, having alkylatable phenol or amine groups, with cation resins having reactive groups.

In a third process, the dyes according to the present invention can be obtained by reacting a dialkylatable amino compound or mixture of compounds with other bi-functional derivatives whose functions can react with an amine, one of the two reacting compounds being a CGCC. These functions can, for example, be epoxides, halides or double activated bonds.

In the aforementioned first process, cation resins such as polyamines or polyamino amides can be used, e.g. Commercial resins can also be used, such as polyethyleneimines. All of these resins have primary, secondary or tertiary alkylatable amine groups capable of reacting with reactive CGCCs, especially CGCCs with mobile chlorine or bromine atoms, epoxy groups or double activated bonds.

In a first variation of this first process, the starting receive molecules that will react with the cation resin have one or several —NHCOCH$_2$Cl radicals. Preferably, these molecules are compounds resulting from the chloroacetylation of dyes having one or several aromatic amine functions replaced by an aminoalkyl radical or having one or several aminoalkoxy substitutions, it being understood that only the extra-nuclear amine functions are chloroacetylated. These chloroacetylated reactive compounds can belong to various large categories of dyes and can be obtained, for example, by chloroacetylation of nitro benzene dyes, anthraquinone dyes, azo dyes, indamines, indoanilines, indophenols, 1,4-benzoquinone dyes such as those described in U.S. Pat. Nos. 3,919,265 and 4,023,926 and U.S. patent application Ser. No. 762,272, which describe the dyes as follows:

The present invention relates to new 2.5-diamino-1,4-benzoquinones of the formula:

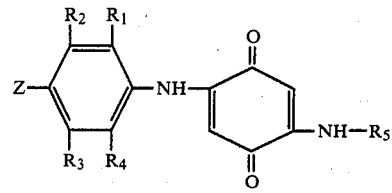 (I)

wherein $R_1$, $R_2$, $R_3$ and $R_4$ each independently represent a member selected from the group consisting of hydrogen, halogen, lower alkyl having 1–4 carbon atoms and lower alkoxy having 1–4 carbon atoms; $R_5$ represents a member selected from the group consisting of hydrogen, lower alkyl containing 1–4 carbon atoms and lower alkyl having 1–4 carbon atoms and substituted with a member selected from the group consisting of hydroxyl and

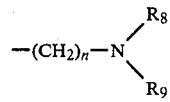

wherein n is 2–6 and preferably 2, and $R_8$ and $R_9$ each independently are selected from the group consisting of hydrogen, alkyl having 1–4 carbon atoms and alkyl having 1–4 carbon atoms and substituted by a member selected from the group consisting of hydroxy and acylamino wherein the acyl is aliphatic having 2–5 carbon atoms or $R_8$ and $R_9$ together with the nitrogen atom to which they are attached form a six-membered heterocycle capable of including an oxygen heteroatom such as piperidinyl or morpholinyl; and Z represents a member selected from the group consisting of hydroxyl,

wherein $R_6$ and $R_7$ each independently represent a member selected from the group consisting of hydrogen, lower alkyl having 1–4 carbon atoms and lower alkyl having 1–4 carbon atoms and substituted by a member selected from the group consisting of hydroxyl, carbamyl, acylamino wherein acyl has the meaning given above, mesylamino and benzoylamino, and

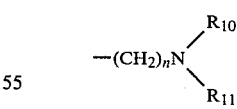

wherein n represents 2–6, preferably 2, and $R_{10}$ and $R_{11}$ each independently represent a member selected from the group consisting of lower alkyl having 1–4 carbon atoms, lower alkyl having 1–4 carbon atoms and substituted by a member selected from the group consisting of hydroxyl and acylamino wherein acyl has the meaning given above, and $R_{10}$ and $R_{11}$ together with the nitrogen atom to which they are attached form a six-membered heterocycly capable of including an oxygen heteroatom, such as piperidinyl or morpholinyl.
U.S. Pat. No. 3,919,265

The present invention also relates to the salts of the compounds of formula I with mineral or organic acids such as the hydrochloride, hydrobromide, and sulfate thereof and to the quaternary ammonium salts of those compounds which have a tertiary amino group.

The compounds of the present invention can be prepared by condensing a 3-amino-4-methoxy phenol of the formula

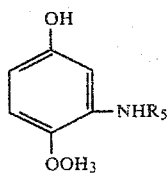

wherein $R_5$ has the meaning given above or on a salt of said compound formed with a mineral or organic acid, on a member selected from the group consisting of a. a compound of the formula

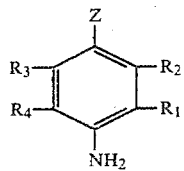

wherein Z, $R_1$, $R_2$, $R_3$ and $R_4$ have the meanings given above, or a salt of said compound, the molar ratio of compounds III/II being preferably between 0.75–1.75, the condensation being carried out at a temperature between 5°–40° C. at atmospheric pressure;

b. a benzoquinone-monoimine or diimine of the formula:

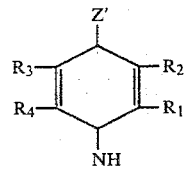

wherein Z' represents a member selected from the group consisting of oxygen or imine and $R_1$, $R_2$, $R_3$ and $R_4$ have the meanings given above with the proviso that at least two of $R_1$, $R_2$, $R_3$ and $R_4$ are other than hydrogen. The condensation is carried out, preferably, at a temperature between 5°–40° C. at atmospheric pressure. The molar ratio of compound IV/II is preferably equal to 1; and c. a nitroso derivatives of the formula:

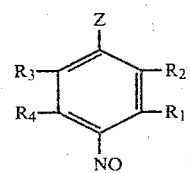

or a salt thereof, wherein Z, $R_1$, $R_2$, $R_3$ and $R_4$ have the meanings given above, the condensation being carried out, preferably, at a temperature between 15°–80° C. at atmospheric pressure, the molar ratio of compounds V/II being between 1–1.5.

U.S. Pat. No. 4,023,926

This is a division of application Ser. No. 370,737 filed June 18, 1973 now U.S. Pat. No. 3,919,265.

Ser. No. 762,272 (now U.S. Pat. No. 4,084,052)

The present invention relates to new 2,5-diamino-1,4-benzoquinones of the formula:

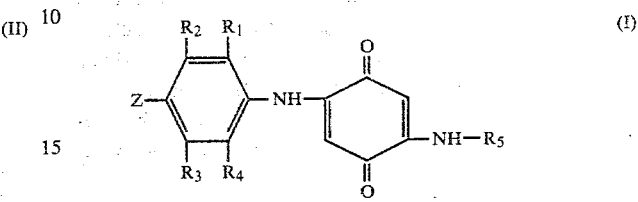

wherein $R_1$, $R_2$, $R_3$ and $R_4$, each independently represent a member selected from the group consisting of hydrogen, halogen, lower alkyl having 1–4 carbon atoms and lower alkoxy having 1–4 carbon atoms; $R_5$ represents a member selected from the group consisting of hydrogen, lower alkyl containing 1–4 carbon atoms and lower alkyl having 1–4 carbon atoms and substituted with a member selected from the group consisting of hydroxyl and

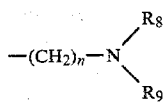

wherein n is 2–6 and preferably 2, and $R_8$ and $R_9$ each independently are selected from the group consisting of hydrogen, alkyl having 1–4 carbon atoms and alkyl having 1–4 carbon atoms and substituted by a member selected from the group consisting of hydroxy and acylamino wherein the acyl is aliphatic having 2–5 carbon atoms or $R_8$ and $R_9$ together with the nitrogen atom to which they are attached form a six-membered heterocycle capable of including an oxygen heteroatom such as piperidinyl or morpholinyl; and Z represents a member selected from the group consisting of hydroxyl,

wherein $R_6$ and $R_7$ each independently represent a member selected from the group consisting of hydrogen, lower alkyl having 1–4 carbon atoms and lower alkyl having 1–4 carbon atoms and substituted by a member selected from the group consisting of hydroxyl, carbamyl, acylamino wherein acyl has the meaning given above, mesylamino and benzoylamino, and

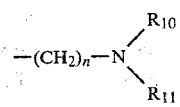

wherein n represents 2–6, preferably 2, and $R_{10}$ and $R_{11}$ each independently represent a member selected from the group consisting of lower alkyl having 1–4 carbon atoms, lower alkyl having 1–4 carbon atoms and substituted by a member selected from the group consisting of hydroxyl and acylamino wherein acyl has the meaning given above, and $R_{10}$ and $R_{11}$ together with the nitrogen atom to which they are attached form a six-membered heterocycle capable of including an oxygen heteroatom, such as piperidinyl or morpholinyl.

The present invention also relates to the salts of the compounds of formula I with mineral or organic acids such as the hydrochloride, hydrobromide, and sulfate thereof and to the quaternary ammonium salts of those compounds which have a tertiary amino group.

The compounds of the present invention can be prepared by condensing a 3-amino-4-methoxy phenol of the formula

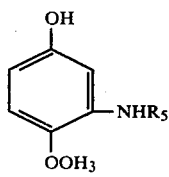

wherein $R_5$ has the meaning given above or on a salt of said compound formed with a mineral or organic acid, on a member selected from the group consisting of (a) a compound of the formula

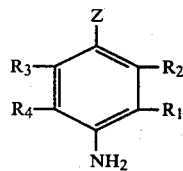

wherein Z, $R_1$, $R_2$, $R_3$ and $R_4$ have the meanings given above, or a salt of said compound, the molar ratio of compounds III/II being preferably between 0.75–1.75, the condensation being carried out at a temperature between 5°–40° C. at atmospheric pressure;

(b) a benzoquinone-monoimine or diimine of the formula:

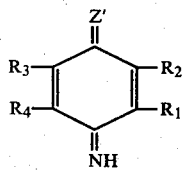

wherein Z' represents a member selected from the group consisting of oxygen or imine and $R_1$, $R_2$, $R_3$ and $R_4$ have the meanings given above with the proviso that at least two of $R_1$, $R_2$, $R_3$ and $R_4$ are other than hydrogen. The condensation is carried out, preferably, at a temperature between 5°–40° C. at atmospheric pressure. The molar ratio of compounds IV/II is preferably equal to 1; and (c) a nitroso derivative of the formula:

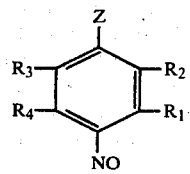

or a salt thereof, wherein Z, $R_1$, $R_2$, $R_3$ and $R_4$ have the meanings given above, the condensation being carried out, preferably, at a temperature between 15°–80° C. at atmospheric pressure, the molar ratio of compounds V/II being between 1–1.5.

Representative nitro benzene dyes include reactive dyes obtained by chloroacetylation of ortho-, meta- and paranitraniline derivatives such as 3-nitro 4-N-β-aminoethylaminoanisole of Example 4 of U.S. Pat. No. 3,617,163, (melting point of the chloroacetylated derivative = 118°–119° C.); 3-nitro-6-amino phenoxyethylamine of Example 9 of French patent application No. 74-36651; 3-nitro 4-amino-phenoxyethylamine, Example 13 of French patent No. 74-36651; 4-nitro N-β-aminoethylaniline (melting point of the chloroacetylated derivative = 142° C.); or, by chloroacetylation of nitropara (or meta) phenylenediamine derivative such as 1-N-β-aminoethylamino-3-nitro-4-N'-methylamino benzene, Example 27 of U.S. Pat. No. 3,665,036; 1-N,N-di-β-hydroxyethylamino-3-nitro-4-N'-β-aminoethylamino benzene, Example 20 of French patent No. 1,506,350; 1-methylamino-2-nitro-4-(N'-methyl, N'-β-aminoethyl) amino benzene, Examples 5 and 6 of French patent No. 1,506,350 (melting point of the chloroacetylated derivative = 140° C.); or 1-dimethylamino-3-N-β-aminoethylamino 4-nitro benzene, Example 5 of U.S. Pat. No. 3,560,136 (melting point of the chloroacetylated derivative = 148° C.).

Representative anthraquinone chloroacetylated dyes include 1-γ-chloroacetylamino propylamino anthraquinone (melting point = 183° C.) obtained by chloroacetylation of 1-γ-aminopropyl amino anthraquinone, Example 3 of British Pat. No. 1,159,557, or 1-γ-chloroacetylaminopropyl amino 4-N-methyl amino anthraquinone (melting point = 215° C.) obtained by chloroacetylation of the product described in Example 2 of British Pat. No. 1,159,557; or 1-hydroxy-4-γ-chloroacetylaminopropyl amino anthraquinone (melting point = 175° C.) obtained by chloroacetylation of the product described in British Pat. No. 1,227,825, corresponding to U.S. Pat. Nos. 3,576,587 and 3,806,525; or 2-β-chloroacetylaminoethyl amino anthraquinone (melting point = 210° C.) obtained by chloroacetylation of the product described in Example 7 of British Pat. No. 1,159,557. In these examples, the chloroacetylation of the anthraquinone initial reactant is carried out preferably in dioxane in the presence of sodium carbonate. For the first three anthraquinone compounds mentioned above, the amine functions are chloroacetylated as a whole, followed by a selective dealkylation using sulfuric acid. For the fourth anthraquinone compound mentioned above, the extra-nuclear amine function is selectively chloroacetylated.

Representative useful chloroacetylated azo compounds are obtained by coupling diazonium salts with N-ethyl-N-β-chloroacetylaminoethylaniline. As examples, there are the azo compounds of 2-amino benzothiazole and of N-ethyl N-β-chloroacetylaminoethylaniline (melting point = 178° C.).

Representative chloroacetylated derivatives of indamines, indoanilines and indophenols include N-[[4-(ethyl β-chloroacetylaminoethyl)amino]phenyl] 2,6-dimethyl 3-amino benzoquinone imine (melting point 156° C.) obtained by reacting 4-nitroso N-ethyl N-β-chloroacetylaminoethyl aniline with 2,6-dimethyl 3-amino phenol.

Representative chloroacetylated 1,41-benzoquinone dyes include 2-N-β-hydroxyethyl amino-5-(4-N-ethyl, N-β-β-chloroacetylaminoethyl amino anilino)-1,4-benzoquinone (melting point=160° C.) obtained by reacting 4-nitroso N-ethyl, N-β-chloroacetylaminoethyl aniline with 3-β-hydroxyethyl amino 4-methoxy phenol in an ammonia medium in the presence of H₂O₂.

Representative chloroacetylated derivatives of the dyes described in U.S. Pat. No. 3,817,698, which describes that:

A dye composition for dyeing keratinic fibers comprises an aqueous solution of a dye having one of the following formulas:

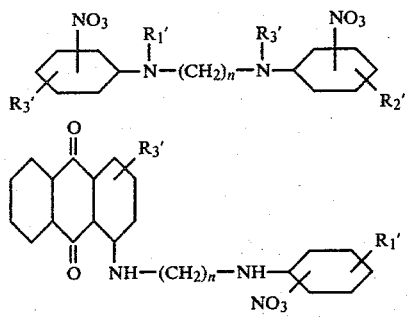

and

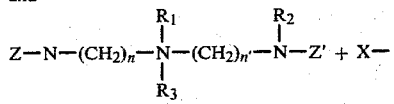

wherein R'₁ and R'₂ are hydrogen, lower alkyl, hydroxy lower alkyl and lower alkyl amino lower alkyl; R'₃ is hydrogen, lower alkoxy and

wherein R'₄ and R'₅ are hydrogen, lower alkyl, hydroxy lower alkyl, lower alkylamino lower alkyl and amino lower alkyl; R'₆ is hydrogen, lower alkoxy and

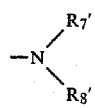

wherein R'₇ and R'₈ are hydrogen, lower alkyl, hydroxy lower alkyl and amino lower alkyl; R'₁₀ is

wherein r" and r''' are hydrogen and lower alkyl; R'₀ is

wherein R₁₁ and R₁₂ are lower alkyl and amino lower alkyl; Z and Z' are dimethylamino nitro phenyl and nitro phenyl; R, R₁, R₂ and R₃ are hydrogen and lower alkyl, n in formulas (1) and (2) is 2–4 and n and n' in formula (3) is 2–6; and X is halogen. The dye is present in amounts of 0.1–3 percent by weight of the composition and after being applied to the hair is left thereon for a period of about 4–30 minutes at a temperature between 15°–35° C., followed by rinsing, washing and drying the hair.

The compound compounds include:
N-[(3 nitro-4-β-chloroacetylaminoethyl amino)phenyl] N'-[(4'-nitro)phenyl]ethylene-diamine resulting from the chloroacetylation of the compound described in Example 17 of French patent No. 1,540,423; or 1-methylamino-γ-[(2'-nitro-5-N-ethyl N-β-chloroacetylamino ethyl amino)phenyl]-4-aminopropyl amino anthraquinone resulting from chloroacetylation of the compound described in Example 19 of French patent No. 1,540,423.

The present invention also relates to the new compound of the formula:

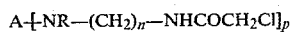

wherein R is alkyl having 1 to 3 carbon atoms; p is a whole number between 1 and 3 inclusive; n is a whole number between 1 and 4 inclusive, wherein the values of n for each of the chloroacetylated p groups attached to nucleus A can be equal or different; and A represents a substituted or nonsubstituted residue of a nitrobenzene dye, an anthraquinone dye, an azo dye, an indamine, an indoaniline, an indophenol, a 1,4-benzoquinone dye or an A-B dye derived from the joining through covalence of two compounds A and B which are dyes, per se, or dye-generators of the benzene, anthraquinone or azo series.

In a second variation of the first process according to the present invention, the colored initial reactant has either one or several aromatic amines replaced by ω-halogenoalkyl, 3-chloro 2-hydroxy propyl or 2,3-epoxy radicals, or halogenoalkoxy groups on an aromatic nucleus. Representative compounds include 1-β-chloroethyl-amino-3-nitro-4-N-methyl amino benzene [Example 2 of British Pat. No. 1,164,825; 1-N-ethyl N-β-chloroethyl 6-amino-3-nitro 4-N'-methyl amino benzene (Example 3 of British Pat. No. 1,164,825), 1-N-β-bromoethyl amino-3-N'-dimethyl amino-4-nitro benzene (Example 18 of French patent No. 1,540,423); (3-nitro 4-amino) phenyl bromoethylether obtained by deacetylation of (3-nitro-4-acetylamino) phenyl bromoethyl ether described in Example 13 of French patent No. 74-36651, corresponding to U.S. patent application Ser. No. 628,999, 1-(3-chloro-2-hydroxy propyl) amino anthraquinone; or 1-(2,3-epoxy propyl)1-amino anthraquinone.

In a third variation of the first process according to the present invention, colored reactive compounds can be used which have chlorotriazinine groups such as in commercial products known under the tradename "Procion", e.g. those corresponding to the formulas given in Color Index and numbered 13245, 13190, 18105 and 18159.

In a fourth variation of the first process according to the present invention, it is possible to use reactive colored compounds having a double activated bond, such as the products known under the tradename "Remazol", for example the vinylsulphones of dyes corresponding to the formulas indicated in Color Index by references 18852 or 61200.

In the second process according to the present invention it is advantageous to use, colored compounds having a phenol or amine group which can be alkylated without appreciably attenuating the dyeing power and in particular, the compounds which were mentioned for the first and second variations of the first process (it being understood that these are compounds before chloroacetylation or halogenoalkylation). As cation resins having reactive groups, the reaction products of an epihalohydrin can advantageously be used (epichlorohydrin or epibromohydrin) with the polyamino-amides resulting from the polycondensation of a diacid and a polyamine of the type:

$$H_2N-[CH_2-CH_2NH]_n-H$$

wherein n has a value of 2 or 3. Representative polyamino-amides include those disclosed in French Pat. No. 74-39242. When the epihalohydrin is used in proportions of from about 0.8–1.3:1 compared to the basic groups, a resin is obtained which may include azetidinium, halohydrin or epoxide groups, all of said groups alkylating amines or phenols and thus making it possible to fix, by covalent bond, colored compounds with an amine or phenol function. The alkylating reactive groups of the resin, which do not react with the colored compounds, can be eliminated by reaction with a nucleophilic compound such as an amine or a mercaptan, for example, or may be maintained in order to increase still further the fixation of the colored polymer onto the substrate to be dyed.

In the third process of the present invention, there can be used colored compounds of the Z—$NH_2$ type as dialkylatable derivatives in polycondensation reactions with dihalogenated, di-epoxide or di-unsaturated derivatives with double activated bonds. In this case, in addition to colored Z—$NH_2$ compounds, another bi-secondary derivative is preferably used, for example piperazine, to increase the water-solubility of the product obtained as well as its affinity for keratinic fibers. It is also possible to use di-halogeno-alkane or di-halohydrin derivatives of colored compounds with secondary or tertiary diamines. This type of reaction is described in French Pat. No. 75-15161, corresponding to U.S. patent application, Ser. No. 577,835 which describes that:

Quaternized polymer selected from
(a) a polymer having recurring units of the formula

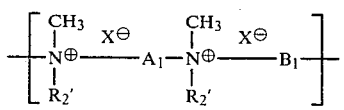

IIA wherein
$A_1$ is
(i) A, wherein A is

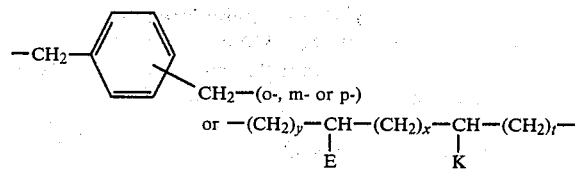

or $-(CH_2)_y-\underset{E}{CH}-(CH_2)_x-\underset{K}{CH}-(CH_2)_t-$ wherein x, y and t are whole numbers ranging from 0 to 11 and being such that the sum $(x+y+t)$ is greater or equal to 0 and less than 18, and E and K represent hydrogen or an aliphatic radical having less than 18 carbon atoms, (ii) $-(CH_2)_n-O-(CH_2)_n-$,
(iii) $-(CH_2)_n-S-(CH_2)_n-$,
(iv) $-(CH_2)_n-S-S-(CH_2)_n-$,
(v) $-(CH_2)_n-SO-(CH_2)_n-$ and
(vi) $-(CH_2)_n-SO_2-(CH_2)_n-$, wherein n is a whole number equal to 2 or 3;

$X^\ominus$ is an anion derived from a mineral or organic acid;

$R'_2$ is an aliphatic, alicyclic or arylaliphatic group containing a maximum of 20 carbon atoms; and $B_1$ is

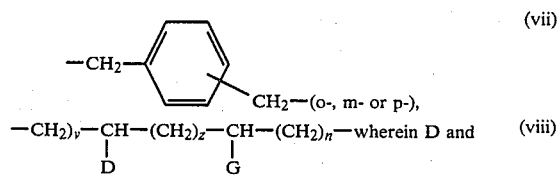

(vii)

$-(CH_2)_v-\underset{D}{CH}-(CH_2)_z-\underset{G}{CH}-(CH_2)_n-$ wherein D and (viii)

G each independently are hydrogen or an aliphatic radical containing less than 18 carbon atoms, and v, z and u are whole numbers ranging from 0 to 11, two of them being able to be simultaneously equal to 0 such that the sum $(v+z+u)$ is lower than 18 and such that the sum $(v+z+u)$ is greater than 1 when the sum $(x+y+t)$ is equal to 0,

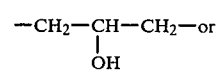

(ix)

(x) $-(CH_2)_n-O-(CH_2)_n-$ wherein n has the meaning given above; with the proviso that $R'_2$ has at least 3 carbon atoms either in the case where $A_1$ or $B_1$ represents $-(CH_2)_n-O-(CH_2)_n-$, or in the case where simultaneously $A_1=A$ and $B_1=B$;

(b) a polymer having recurring units of the formula

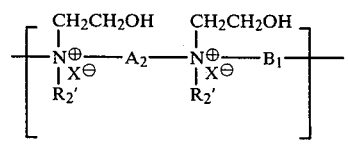

wherein
$A_2$ is
(i') A, which has the meaning given above,
(ii') $-(CH_2)_n-O-(CH_2)_n-$,
(iii') $-(CH_2)_n-S-(CH_2)_n-$, (iv') —$(CH_2)_n$—S—S—$(CH_2)_n$—,
(v') —$(CH_2)_n$—SO—$(CH_2)_n$— and

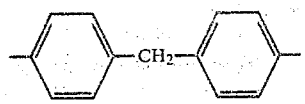
(vi')

wherein n, X, R'$_2$ and B$_1$ have the meanings given above; and (c) a polymer having recurring units of the formula

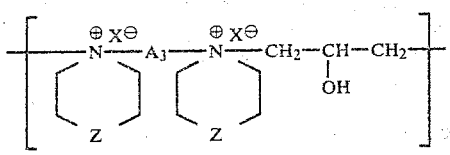
IIC wherein
Z is —O— or —CH$_2$,
A$_3$ is A or —$(CH_2)_n$—O—$(CH_2)_n$—, wherein A has the meaning given above; and
X and n have the meanings given above.

The polymers are usefully employed in cosmetic composition for application to the hair or skin.

Representative bifunctional derivatives that can be used to react with the aminated compounds include the derivatives of piperazine such as N,N'di-(3-chloro-2-hydroxy propyl)-piperazine, N,N'di-(2,3-epoxy propyl)-piperazine, di-acryloyl-piperazine, diglycidyl ether or ethylene-diamine di-acrylamide; colored di-amino derivatives can also be used with bifunctional derivatives such as those which have just been mentioned, or colored di-halogenated derivatives with disecondary amines.

For the above first and second processes, the reactions for preparing the halogenated derivatives or reactive epoxides are generally carried out in a solvent, with or without the presence of water, at temperatures ranging between 0° and 100° C., but preferably between 30° and 70° C. Solvents that can be used are, in particular, the lower alcohols such as methanol, ethanol, isopropanol, t-butanol, alkoxyethanols, aromatic solvents such as benzene or toluene, or other solvents such as dimethylformamide or acetonitrile. The reactions of the reactive colored compounds with the cation resins are most often carried out in the presence of solvents such as those just mentioned, at temperatures ranging between 30° and 130° C., but preferably between 50° and 90° C. The reaction time generally ranges between about 1 to 10 hours. These reactions can be effected on linear or reticulated cation resins, but it is also possible to crosslink the cationic resins with bifunctional derivatives after grafting the colored compound. The colored resins are then precipitated in a non-solvent such as acetone, methylethylketone, methylisobutylketone, or hydrocarbons such as hexane or heptane. Given the reactivity of the colored compounds which, in addition, are in the presence of a considerable surplus of reactive sites on the resins, and given the possibility of precipitating the colored matter, it is in general relatively easy to purify the colored compounds obtained according to the present invention and, especially, to eliminate those dyes or dye precursors which may not have been condensed on the resin. When the colored material cannot be precipitated, the product obtained can be purified by dialysis after solubilization in water. When colored compounds with amino or phenol groups are made to react with reactive resins, the reactions occur in a solvent or in water. When attempting to conserve the reactive resins, they are acidified with, for example, hydrochloric acid before they are isolated. If, on the contrary, one does not wish to conserve the reactive resins, a nucleophilic compound is added, such as an amine or a mercaptan, to consume the normal reaction sites.

The reactions of the third process according to the present invention can be carried out in water, in solvents or in water-solvent mixtures. These reactions occur at temperatures ranging between 50° and 150° C., and preferably between 80° and 130° C. The reaction time is between approximately 1 and 10 hours.

As indicated previously, the colored compounds according to the present invention have a strong affinity for keratinic substrates. Consequently, they can be used in hair dye compositions. Therefore, another object of the present invention is a dye composition intended for dyeing keratinic material such as hair, wool, fingernails or leather, said composition characterized by the fact that it contains in solution at least one colored polymer as defined above.

An initial advantage of the dye compositions according to the present invention is the possibility of using colored compounds which, normally, do not "ride" on substrates such as hair, wool or leather, by imparting to them an affinity for the substrates by means of the aminated groups of the cationic polymer and by increasing their solubility in the dye composition.

Another advantage of the compositions according to the present invention is the possibility of obtaining a shade which is identical or very similar to that of the CGCC which is grafted to obtain the cationic polymer according to the invention. However, it is also possible to obtain different, lasting shades when different CGCCs are used simultaneously for preparing the same cationic colored polymer according to the invention. In this case, there are no different shades of the same color to be noted for the various color generators present, thus making it possible to obtain a good degree of shade consistency and stability. Moreover, since the colored polymer according to the present invention behaves as a color heightening retardant on the substrate, there is generally no need to add a stabilizing agent to the compositions of the invention.

When the compounds according to the present invention are used for dyeing keratinic fibers and, in particular, hair, they offer the advantage of being usable in water. Furthermore, the dye compositions according to the invention are shampoo-proof, whether they be nonionic, cationic or anionic shampoos. Finally, the compositions according to the present invention are advantageous in that they are deposited on the periphery or surface of the fiber, which offers the possibility of a purely surface treatment which does not modify the internal nature of the fiber. In view of the fact that there is no penetration of dye within the fiber, the dye removal operation which precedes a new dyeing operation is facilitated and becomes total; the dye removal is done with oxidizing agents or solvents, as described earlier.

The affinity of the colored polymer for keratinic fibers increases as the fibers become sensitized. However, the compositions according to the present invention have but a very weak affinity for the skin, so that their use results in essentially no coloring of the scalp or hands of the person applying the compositions to the hair.

Moreover, since the molecular weight of the colored polymer of the present invention is several times higher than that of a traditional type dye, diffusion through the skin is considerably reduced, causing almost total disappearance of the toxicity of the colored compounds, dyes or dye precursors which are present within the cationic polymer of the invention. The result is that the compositions of the present invention, which in their free state can be free of dye, are particularly safe with regard to toxicity.

If the colored polymers according to the present invention are prepared by modifying a cationic resin, the resin is generally selected from among resins known for their hair conditioning properties or their fabric finishing properties. It has been noted that in general when there is limited modification of the initial polymer, the colored polymer of the present invention has many of the properties of the original non-colored resin. This means that the compositions of the present invention make it possible to obtain, in addition to coloration of the substrates, effects such as the untangling of fibers, shine, softness and strengthening of the substrate, depending on the effects inherent in the initial cationic resin.

A fundamental characteristic of the dye compositions according to the present invention is the affinity of the cationic polymer of this invention for keratinic substrates such as hair, wool, furs and fingernails, particularly when these substrates are sensitized. The affinity for the keratinic substrates is mainly a function of the cationic function of the resin, thus, of the percentage of colored compound molecules in relation to the aminated groups of the initial resin. This percentage advantageously ranges between 5 and 100%, and preferably between 10 and 40%. It is noteworthy that the lower this percentage, the more the properties of the colored compound of the invention resemble those of the original cationic resin. In addition, the speed of take up onto the hair increases when the percentage decreases.

The use of the compositions according to the present invention for keratinic fibers imparts to said fibers a certain rigidity and a better hold than that which results when dyeing is done with a traditional-type dye. This result is particularly useful for dyeing hair and for dyeing wool, where a decrease in felting is noted.

The dye compositions according to the present invention can contain one or several water-soluble cationic polymers of the invention. In general, the cationic polymers according to the invention are present in a proportion ranging between 0.01% and 10% and, preferably, between 0.02% and 8% by weight with respect to the total weight of the composition. The pH of the composition is between 1 and 11, and preferably, between 3 and 10. When the compositions according to the invention are used for dyeing hair, the contact time can vary between 1 and 30 minutes, it being understood that for lotions applied as hair rinses, there is no prolonged contact time, the said lotion being applied, perhaps rinsed and then dried.

In addition to the cationic polymer compounds of the invention, the compositions according to the invention can contain other dyes, particularly azo dyes, anthraquinone dyes, nitrobenzene dyes, 2,5-diaminoquinones, indophenols, indoanilines, indamines, phenylamines and oxidation bases and couplers.

The compositions according to the present invention are provided in the form of an aqueous solution, possibly mixed with alkalizing or acidifying agents and/or solvents and/or polymers and/or cation type treatment products and/or amides and/or thickeners and/or surfactants and/or additives customarily used in hair cosmetics such as sun filters, optical blueing agents, antioxidizing agents, sequesterants and perfumes. The compositions according to the present invention can also contain oxidation agents.

Representative alkalizing agents include mono- or triethanolamine, ammonium hydroxide, sodium phosphate or sodium carbonate. Representative acidifying agents include phosphoric, hydrochloric, lactic, tartaric, acetic or citric acids. These alkalizing or acidifying agents are employed to adjust the pH of the dye compositions to the aforementioned values.

Representative solvents used in the compositions according to the present invention include low molecular weight alcohols having from 2 to 4 carbon atoms, such as ethyl alcohol or isopropyl alcohol or glycols such as ethylene glycol, propylene glycol or butylene glycol, or glycol ethers such as the methyl ether, ethyl ether or butyl ether of ethylene glycol. The aforementioned solvents are present in amounts ranging between 0.5 and 50% by weight and, preferably, between 1 and 15% by weight relative to the total weight of the composition.

The additional polymers contained in the composition according to the present invention can be polymers or copolymers of vinylpyrrolidone, crotonic acid/vinyl acetate, vinylpyrrolidone/vinyl acetate, cationic polymers such as quaternized polyvinylpyrrolidone polymers, quaternized cellulose derivatives, copolymers of N-vinylpyrrolidone/dimethylaminoethyl methacrylate and polyethylene glycol, quaternized by dimethyl sulphate, crosslinked or not.

These additional polymers are employed in concentrations ranging between 0.1 and 3% by weight and, preferably, between 0.3 and 2% by weight, with respect to the total weight of the composition.

The amides contained in the compositions according to the invention may be fatty acid mono- or diethanolamides, oxyethylenated if need be.

The thickeners can be cellulose derivatives such as carboxymethyl cellulose, hydroxypropylmethyl cellulose or hydroxyethyl cellulose.

The surfactants can be anionic, cationic, non-ionic or amphoteric agents such as sulphates, ether-sulphates, fatty alcohol sulphonates, oxyethylenated fatty acids or alcohols, oxyethylenated alkylphenols, amines and quaternary ammonium salts.

In the compositions according to the invention, the oxidation agents can be $H_2O_2$, carbamide peroxide or persalts such as ammonium persulphate. These oxidation agents are present in a proportion ranging between 1 to 6% by weight with respect to the total weight of the composition.

The compositions according to the invention can be in the form of a gel, cream, foaming or milky liquid, and packaged in flasks, tubes or aerosols.

The following non-limiting examples are given to illustrate the present invention. Unless otherwise stated, all parts and percentages are by weight.

EXAMPLE 1

In 80 cc of a 20:10 mixture of dimethylformamide/methyl "Cellosolve," 13.8 g (basic equivalent, 0.073) of the following polyamino-amide are dissolved, the preparation of which is described in French patent No. 74-39242:

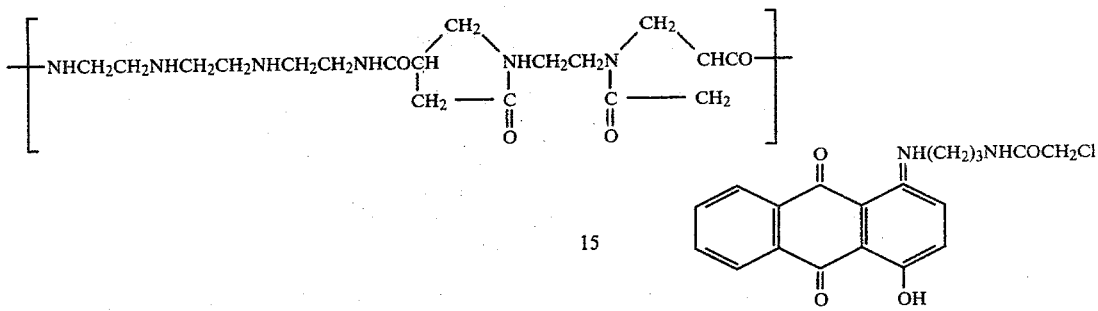

To this mixture, there are quickly added 12.4 g (0.035 mole) of colored compound of the formula:

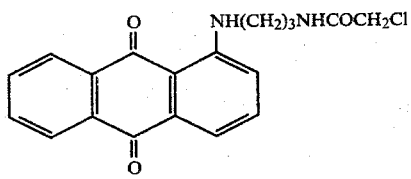

dissolved hot in 100 cc of dimethylformamide.

The resulting solution is heated for 4 hours at 70° C., then neutralized with 23 g of sodium methylate in a methanol solution (0.027 mole) and heated again for 2 hours at the same temperature.

The resulting polymer is isolated from its solution by precipitation in 2 liters of acetone. It is a red, powdery solid. Its proportion of condensed colored compound, measured by spectroscopy, is 34% by weight (wave length of maximum absorption, $\lambda_{max}=500$ nm).

Thin layer chromatography is used to verify that the colored polymer no longer contains any detectable amount of initial colored compound.

EXAMPLE 2

In 60 cc of a 20:40 mixture of dimethylformamide/-methyl "Cellosolve," 63 g (basic equivalent 0.34) of the following polymer are dissolved, the preparation of which is described in French Patent No. 74-39 242:

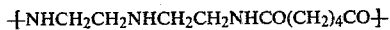

To this solution there are added 12 g (0.034 mole) of the chloroacetylated derivative used in Example 1, dissolved in 100 cc of dimethylformamide.

The resulting mixture is heated for 6½ hours, then poured drop by drop into 3 liters of acetone. The resulting polymer precipitates as a gum. It is taken up in a 30:30 DMF/MC mixture, then re-precipitated in the acetone. A soft resin is isolated with a yield of 87%.

Its proportion of condensed colored compound, measured by spectroscopy, is 12.2% by weight ($\lambda_{max}=500$ nm).

EXAMPLE 3

To 30 cc of a 10:20 DMF/MC mixture containing 24.85 g (basic equivalent 0.134) of the resin described in Example 2, 100 cc of DMF solution are added, containing 10 g (0.027 mole) of compound having the formula:

The resulting mixture is heated for 3½ hours at 60° C., then poured into 3 liters of acetone. A gum is isolated, which is purified by another solubilization and re-precipitation. After drying, a powdery solid is obtained, containing 21.5% by weight of condensed colored compound ($\lambda_{max}=586$ and 549 nm), measured by spectroscopy.

EXAMPLE 4

To 70 cc of a 20:50 DMF/MC mixture containing 33.89 g of the resin described in Example 2, 20 g (0.0547 mole) of the chloroacetylated derivative used in Example 3 are added, dissolved in 100 cc of DMF.

The mixture is heated for 4 hours at 60° C., then concentrated by partial evaporation of the solvent under reduced pressure. The mixture is poured into ½ liter of acetone. The precipitated resin is rinsed several times in acetone.

After drying, a powdery solid is obtained with a yield of 74%, containing 30.5% by weight of condensed colored compound ($\lambda_{max}=586$ nm and 549 nm), measured by spectroscopy.

EXAMPLE 5

To 6 g (basic equivalent 0.0324) of the resin described in Example 2 and dissolved in 10 cc of methyl "Cellosolve", 50 cc of a solution of DMF containing 7.3 g (0.0196 mole) of the chloroacetylated derivative prepared in Example 3 are added. The resulting mixture is then heated for 3 hours at 80° C. Then 1.6 g (0.01 mole) of sodium methylate are added in a methanol solution and heated again for 2 hours at the same temperature. The mixture is then poured into a large excess of acetone.

After drying, a solid is isolated with a yield of 60%, containing 42% of condensed colored compound ($\lambda_{max}=548$ nm and 586 nm), measured by spectroscopy.

EXAMPLE 6

To a solution of 13.86 g (0.0495 mole) of colored compound having the formula:

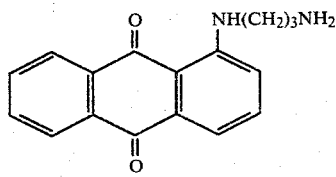

dissolved in 135 g of methyl "Cellosolve", 9.8 g of di(epoxy propyl) piperazine (0.0495 mole) are added. The resulting mixture is then heated for 5 hours at 90° C. The solution is then poured into 1.5 liters of sulfuric ether. A powdery solid is isolated, with an 82% yield, the molecular weight of which is 2960, measured by vapor pressure.

After dialysis, a polymer is isolated with a molecular weight of 3500. It contains 53% by weight of condensed colored compound ($\lambda_{max}=500$ nm).

EXAMPLE 7

To 80 g (basic equivalent 0.432) of the resin described in Example 2, in solution in a 150:45 MC/DMF mixture, a solution of 52 g (0.129 mole) of the following colored compound in 500 cc of DMF is added:

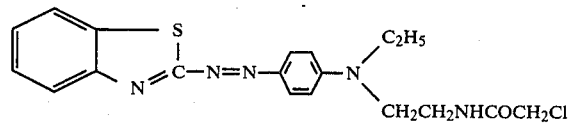

The resulting mixture is heated for 5 hours at 70° C., then concentrated by partial evaporation of the solvent under reduced pressure. The concentrated solution is poured into 4 liters of acetone.

After drying, a hard resin is isolated, containing 30% by weight of condensed colored compound ($\lambda_{max}=505$ nm), measured by spectroscopy.

EXAMPLE 8

A mixture of 11.84 g (0.0598 mole) of di-(epoxy propyl)piperazine and 10 g (0.0598 mole) of a colored compound of the formula:

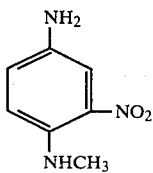

in 50 cc of DMF is heated for 13½ hours at 120° C. The solution is then poured into an extremely large excess of ethanol.

After drying, a powdery solid is isolated, containing 29% by weight of condensed colored compound, measured by spectroscopy.

EXAMPLE 9

A mixture of 19.8 g (0.1 mole) of di-(epoxy propyl) piperazine, 8.35 g (0.05 mole) of a colored compound of the formula:

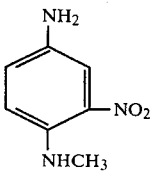

and 4.3 g (0.05 mole) of piperazine in 80 cc of DMF is heated for 12 hours at 120° C. The mixture is then dispersed in 1 liter of acetone.

After drying, a powdery solid is isolated, with a yield of 63%, and containing 11% by weight of condensed colored compound.

EXAMPLE 10

To 17.6 g (basic equivalent 0.095) of the resin described in Example 2, dissolved in 30 cc of MC, 70 cc of DMF are added, containing 8 g (0.019 mole) of a colored compound of the formula:

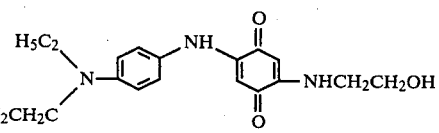

The mixture is heated for 5 hours at 90° C., then precipitated in 1 liter of acetone. After drying, a soft resin is isolated, containing 23% by weight of condensed colored compound ($\lambda_{max}=555$ nm and 425 nm).

EXAMPLE 11

To 30.8 g (basic equivalent 0.167) of the resin described in Example 2, dissolved in 50 cc of MC, 150 cc of DMF are added, containing 19.4 g (0.05 mole) of a colored compound of the formula:

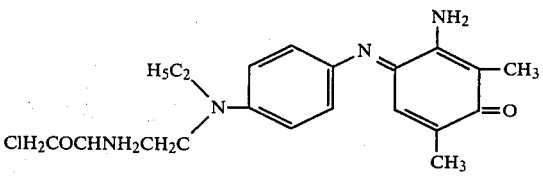

The mixture is heated for 5 hours at 90° C., then poured into a large excess of acetone. After drying, a solid is obtained, containing 22% by weight of condensed colored compound.

EXAMPLE 12

To 3.6 g of the cationic resin used in Example 2 (basic equivalent 0.0195), dissolved in 20 g of DMF, 7.6 g (0.0195 mole) of the following compound are added in solution in the DMF:

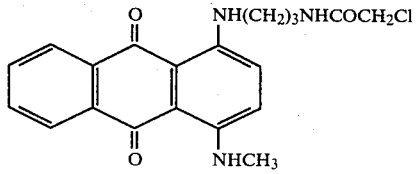

The reaction medium is heated at 80°-90° C. for 8 hours and the appearing acidity is progressively neutralized with a methanol solution of sodium methylate. The resin obtained is precipitated in 2 liters of acetone, then rinsed twice with 1 liter of solvent. There is thus obtained 8.3 g of blue resin soluble in water at a pH $\leq 6.5$.

The quantity of fixed colored compound, determined by spectroscopy, is 37% by weight, with respect to the colored polymer of this invention.

EXAMPLE 13

To 23 g (basic equivalent 0.29) of polyethyleneimine sold by the FLUKA Company under the name "Polymin P", dissolved in 40 g of dimethylformamide, 10 g of the colored compound of Example 1 are added, dissolved in the same solvent, then heated while agitating for 6 hours at 90° C. The colored resin is then isolated by precipitation in 2 liters of acetone.

After two washings with an excess of solvent, a dark red, water-soluble powder is obtained.

EXAMPLE 14

In 65 cc of a 55:10 mixture of DMF/MC, there are dissolved 9.65 g (basic nitrogen equivalent 0.052) of the resin described in Example 2, and 1.87 g (0.0052 mole), 1.65 g (0.0048 mole) and 2.13 g (0.0055 mole), respectively, of the following three colored compounds:

(1) red colored compound ($\lambda_{max}=508$ nm) of the formula:

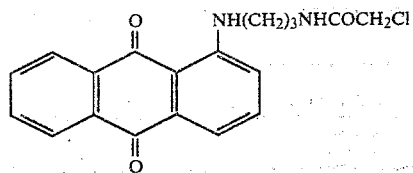

(2) Yellow colored compound ($\lambda_{max}=468$ nm) of the formula:

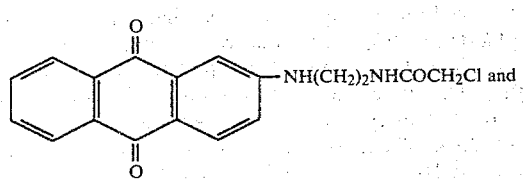

(3) blue colored compound ($\lambda_{max}=575$ and 619 nm) of the formula:

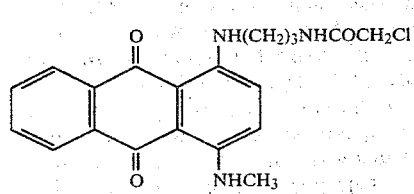

The solution is heated for 5 hours at 90° C. The resulting polymer is isolated by precipitation in 1 liter of acetone, giving a steel-gray solid. Thin layer chromatography is used to check that the colored polymer no longer contains any detectable amount of the initial colored compound. The proportion of condensed colored compound, measured by spectroscopy, is as follows:

| Condensed Colored Compound | Percent by Weight Relative to the Colored Resin |
|---|---|
| Red | 6.28 |
| Yellow | 5.76 |
| Blue | 6.89 |

EXAMPLE 15

In 60 cc of a 45:15 DMF/MC mixture, there are dissolved 16.1 g (basic nitrogen equivalent 0.0869) of the resin described in Example 2 and 5 g (0.0174 mole) of a colored compound having the formula:

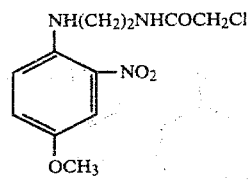

The solution is heated for 5 hours at 90° C., then the resulting polymer is isolated by precipitation in 1 liter of acetone. It is a blue solid ($\lambda_{max}=478$ nm). Thin layer chromatography ensures that the colored polymer no longer contains any initial colored compound. The proportion of initial colored compound in the polymer, measured by spectroscopy, is 17.15% by weight.

EXAMPLE 16

In 90 cc of a basic 80:10 mixture of DMF/MC, there are dissolved 10 g (nitrogen equivalent 0.054) of the resin described in Example 2 and 4.8 g (0.016 mole) of a colored compound of the formula:

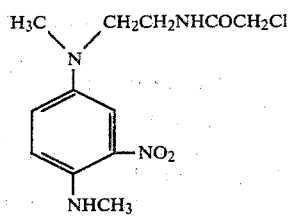

The mixture is heated for 5 hours at 90° C., then the polymer is isolated by precipitation in 1 liter of acetone.

A purple powder is isolated ($\lambda_{max}=527$ nm). Thin layer chromatography reveals the absence of free colored compound. The proportion of initial colored compound in the polymer, measured by spectroscopy, is 22.5% by weight.

EXAMPLE 17

In 135 cc of a 120:15 DMF/MC mixture, there are dissolved 10.5 g (basic nitrogen equivalent 0.0566) of the resin described in Example 2 and 1.8 g (0.0045 mole), 3.3 g (0.011 mole) and 0.6 g (0.0016 mole), respectively, of the following three colored compounds:

(1) red colored compound ($\lambda_{max}=505$ nm) of the formula:

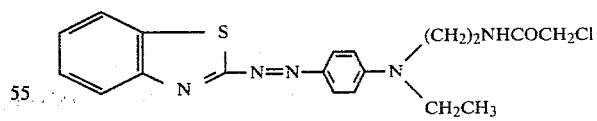

(2) yellow colored compound ($\lambda_{max}=403$ nm) of the formula:

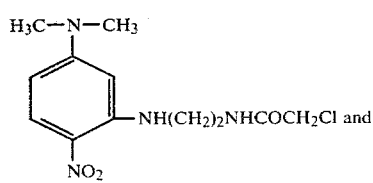

(3) blue colored compound ($\lambda_{max}$=575 and 619 nm) of the formula:

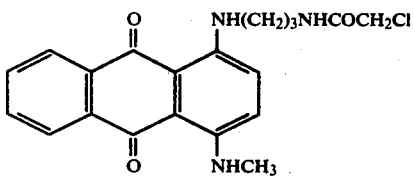

The solution is heated for 5 hours at 90° C., then the resulting colored polymer is precipitated in 500 cc of acetone. After drying, a dark auburn solid is isolated. Thin layer chromatography reveals no initial colored compounds. The proportion of condensed colored compounds in the polymer, measured by spectroscopy, is as follows:

| Condensed Colored Compound | Percent by Weight Relative to the Colored Polymer |
|---|---|
| Red | 7.04 |
| Yellow | 14.2 |
| Blue | 2.1 |

EXAMPLE 18

In 42 cc of a 35:7 DMF/MC mixture, there are dissolved 7.15 g (basic nitrogen equivalent 0.0386) of the resin described in Example 2, and 2.5 g (0.0083 mole), and 1 g (0.0033 mole), respectively, of the following colored compounds:

(1) purple colored compound ($\lambda_{max}$=527 nm) of the formula:

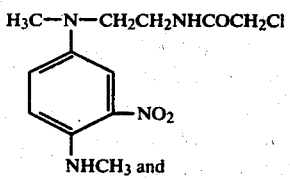

(2) yellow colored compound ($\lambda_{max}$=403 nm) of the formula:

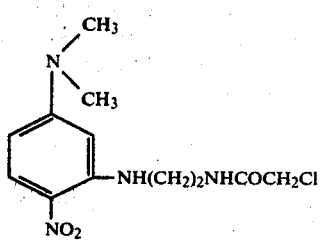

The mixture is heated for 4 hours at 90° C. The resulting polymer is precipitated in 500 cc of acetone. A brown solid, free from initial colored compounds, is obtained as verified by thin layer chromatography. The polymer has the following proportion of condensed colored compounds, measured by spectroscopy:

| Condensed Colored Compound | Percent by Weight Relative to the Colored Polymer |
|---|---|
| Purple | 14.32 |
| Yellow | 6.36 |

EXAMPLE 19

To 576 g of an ethanol solution containing 76.5 g (0.5 mole) of 2-nitroparaphenylenediamine, there are rapidly added 99.9 g (1.08 mole) of epichlorohydrin. The resulting mixture is then heated for 10 hours at solvent reflux. The solvent as well as free epichlorohydrin are removed by evaporation under reduced pressure.

To 30 g of the above synthesized compound, dissolved in 500 cc of methyl "Cellosolve", 56.8 g (0.66 mole) of piperazine in a 50% solution in the same solvent are added. The resulting reaction medium is heated for 3 hours at 90° C. The hydrochloric acid formed is then neutralized with 16.7 g of 40% NaOH. There are then added 46.5 g (0.5 mole) of epichlorohydrin, drop by drop, over a 20 minute period. The reaction medium is then heated for 1½ hours at 90° C.

The resulting polymer is precipitated by the addition of 3 liters of acetone. After drying, a powdery solid, soluble in water at a pH lower than 7.5 is obtained. Thin layer chromatography reveals no free initial colored compound. The proportion of initial colored compound in the polymer, measured by spectroscopy, is 8.79% by weight.

The polymer can be represented by the following formula:

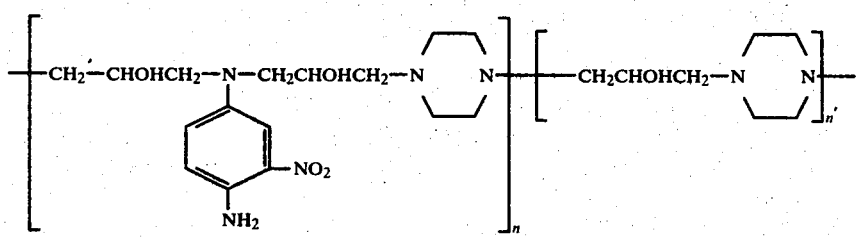

with n/n'=0.17.

EXAMPLE 20

To 2,643 g of an aqueous solution containing 185.2 g (basic equivalent 1) of the polyaminoamide described in Example 2, there are added with stirring, over a 1 hour period at 20° C., 87.9 g (0.95 mole) of epichlorohydrin. The solution is maintained with stirring for 1 hour at that temperature, and then for 1 hour at 90° C.

To 250 g of the above solution, reduced to 125 g by evaporation of the water, there are added 71 g of an acetonitrile solution containing 7.1 g (0.043 mole) of a colored compound having the formula:

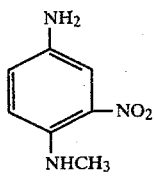

The resulting reaction medium is heated for 3 hours at 80° C. The free colored compound is removed from the aqueous solution by extraction, initially with chloroform and then with ether. After evaporation of the remaining organic solvent, the 5% solution of active material is added to water. Thin layer chromatography reveals no free colored compound. The proportion of fixed colored compound on the polymer, measured by spectroscopy, is 15% by weight.

EXAMPLE 21

In 14 cc of methyl "Cellosolve", 3.6 g (basic equivalent 0.019) of the resin described in Example 2 and 1 g (0.0039 mole) of a colored compound of the following formula are dissolved:

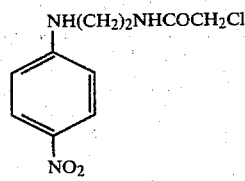

The resulting reaction medium is heated for 5 hours at 90° C. The polymer is isolated by precipitation in acetone. It is a light brown solid ($\lambda_{max}=396$ nm). It is free of initial colored compound as verified by thin layer chromatography. The amount of colored compound in the polymer, measured by spectroscopy, is 18% by weight.

EXAMPLE 22

To 10.2 g of a solution of methyl "Cellosolve" containing 3.06 g (basic equivalent 0.0165) of the resin used in Example 14, there are added 1.225 g (0.005 mole) of N-bromoethyl paranitraniline, dissolved in 20 cc of dimethylformamide. The resulting mixture is heated for 5 hours at 90° C. The resulting polymer is precipitaed in 500 cc of acetone, yielding a yellow polymer ($\lambda_{max}=394$ nm), free of initial colored compound as verified by thin layer chromatography. The polymer contains 15.5% by weight of the initial colored compound, measured by spectroscopy.

EXAMPLE 23

A hair dye composition is prepared by admixing the following components:
Polymer of Example 6: 0.07 g
Polymer of Example 12: 0.055 g
Vinyl acetate crotonic acid copolymer (90:10) M.W. 45,000–50,000: 1.5 g
Vinylpyrrolidone-vinyl acetate copolymer (60:40) viscosity 3.4–4 cps, M.W. 45,000–60,000: 0.25 g
Ethyl alcohol, sufficient for: 50°
Triethanolamine, sufficient for: pH 7
Water, sufficient for: 100 cc This hair setting lotion, when applied to deep blond hair, imparts thereto an especially pleasing pretty dark blond shade.

EXAMPLE 24

A hair dye composition is prepared by admixing the following components:
Polymer of Example 12: 0.0325 g
Vinyl acetate crotonic acid copolymer (90:10) M.W. 45,000–50,000: 1.5 g
Vinylpyrrolidone-vinyl acetate copolymer (60:40) viscosity 3.4–4 cps, M.W. 45,000–60,000: 0.25 g
Ethyl alcohol, sufficient for: 50°
Triethanolamine, sufficient for: pH 7
Water, sufficient for: 100 cc This hair setting lotion, when applied to chestnut colored hair, imparts thereto a very pretty ash-chestnut shade.

EXAMPLE 25

A hair dye composition is prepared by admixing the following components:
Polymer of Example 5: 0.18 g
Vinyl acetate crotonic acid copolymer (90:10) M.W. 45,000–50,000: 1.5 g
Vinylpyrrolidone-vinyl acetate copolymer (60:40) viscosity 3.3–4 cps, M.W. 45,000–60,000: 0.25 g
Ethyl alcohol, sufficient for: 50°
Triethanolamine, sufficient for: pH 7
Water, sufficient for: 100 cc When applied to light chestnut colored hair, this hair-setting lotion imparts to the hair especially attractive iridescent ashen glints.

EXAMPLE 26

A hair dye composition is prepared by admixing the following components:
Polymer of Example 1: 0.04 g
Polymer of Example 5: 0.05 g
Polyvinylpyrrolidone, M.W.=40,000: 0.05 g
Trimethylcetylammonium bromide: 0.2 g
Quaternized polyvinylpyrrolidone, sold under the tradename "GAFQUAT 734" (active matter): 0.4 g
Ethyl alcohol, sufficient for: 12°
Triethanolamine, sufficient for: pH 7
Water, sufficient for: 100 cc This rinse is applied to hair colored very light blond. After drying, the hair untangles easily and has a particularly shiny and esthetic silvery blond shade.

EXAMPLE 27

A hair dye composition is prepared by admixing the following components:
Polymer of Example 2: 0.35 g
Polymer of Example 4: 0.1 g
Vinylpyrrolidone-vinyl acetate copolymer (60:40) viscosity 3.3–4 cps, M.W. 45,000–60,000: 0.5 g
Trimethylcetylammonium bromide: 0.1 g
$H_2O_2$ (20 vol), sufficient for: 10 vol.
Orthophosphoric acid, sufficient for: pH 3
Water, sufficient for: 100 cc When applied to natural deep blond hair, this lotion, after drying, imparts thereto a light sheen with pretty auburn glints.

EXAMPLE 28

A hair dye composition is prepared by admixing the following components:
Polymer of Example 6: 0.5 g
Sodium laurylsulphate with 30% active ingredients sold under the name "DELF 8533": 25 g
Butyl "Cellosolve": 10 g
Copra diethanolamide: 5 g
Citric acid, sufficient for: pH 6
Water, sufficient for: 100 cc Natural light chestnut colored hair, when shampooed with this composition, after rinsing and drying, has very lustrous mahogany glints.

EXAMPLE 29

A hair dye composition is prepared by admixing the following components:
Polymer of Example 12: 0.325 g
Polymer of Example 2: 0.775 g
Trimethylcetylammonium bromide: 5 g
Lauryl alcohol oxyethylenated with 12.5 moles of ethylene oxide, sold under the name "FREPAL 12": 4 g
Citric acid, sufficient for: pH 4
Water, sufficient for: 100 cc Bleached hair, when shampooed for 15 minutes with this composition, after rinsing and drying, has a particularly esthetic looking pearly shade.

EXAMPLE 30

A hair dye composition is prepared by admixing the following components:
Polymer of Example 3: 0.85 g
Hydroxyethylcellulose sold under the name "CELLOSIZE 3": 3.52 g
Citric acid, sufficient for: pH 6
Water, sufficient for: 100 cc When applied for 20 minutes to blond hair, this composition, after rinsing and drying, imparts thereto a very lovely ash-blond shade.

EXAMPLE 31

A hair dye composition is prepared by admixing the following components:
Polymer of Example 2: 7.75 g
Hydroxyethylcellulose sold under the name "CELLOSIZE WP 3": 3.52 g
Citric acid, sufficient for: pH 6
Water, sufficient for: 100 cc When applied for 15 minutes to chestnut colored hair, this composition, after rinsing and drying, imparts thereto very original, pretty rose glints.

EXAMPLE 32

A hair dye composition is prepared by admixing the following components:
Polymer of Example 4: 1 g
Butyl "Cellosolve": 8 g
Propylene glycol: 8 g
Alkylphenol polyethoxyether, sold under the name "REMCOPAL 334": 22 g
Alkylphenol polyethoxyether sold under the name "REMCOPAL 349": 22 g
Ammonia—22° Bé: 10 cc
Water, sufficient for: 100 g Twenty grams of water are added to 20 g of the above solution, giving a gel which is applied to light blond colored hair. The gel is permitted to remain in contact with the hair for 20 minutes. Thereafter the hair is washed. After drying, the hair has very pretty ash-blond glints.

EXAMPLE 33

A hair dye composition is prepared by admixing the following components:
Polymer of Example 1: 2.4 g
Polymer of Example 2: 3.1 g
Polymer of Example 4: 0.25 g
Butyl "Cellosolve": 8 g
Propylene glycol: 8 g
Alkylphenol polyethoxyether, sold under the name "REMCOPAL 334": 22 g
Alkylphenol polyethoxyether, sold under the name "REMCOPAL 349": 22 g
Ammonia—22° Bé: 10 cc
Water, sufficient for: 100 g Twenty grams of water are added to 20 g of the above solution. A gel is obtained that is applied for 30 minutes to deep chestnut colored hair. After rinsing and drying, the hair exhibits particularly esthetic lilac glints.

EXAMPLE 34

A hair dye composition is prepared by admixing the following components:
Polymer of Example 2: 3 g
Polymer of Example 3: 0.3 g
Butyl "Cellosolve": 8 g
Propylene glycol: 8 g
Alkylphenol polyethoxyether, sold under the name "REMCOPAL 334": 22 g
Alkylphenol polyethoxyether, sold under the name "REMCOPAL 349": 22 g
Ammonia—22° Bé: 10 cc
Water, sufficient for: 100 g Twenty grams of $H_2O_2$ (20 volumes) are added to 20 g of the above prepared solution. This gives a gel which is applied to blond hair. After 30 minutes contact time, the hair is washed and becomes lighter in color with a slightly iridescent, lovely pearly luster.

EXAMPLE 35

A hair dye composition is prepared by admixing the following components:
Polymer of Example 16: 0.4 g
Vinyl acetate crotonic acid copolymer (90:10) M.W. 45,000–50,000: 1.5 g
Vinylpyrrolidone-vinyl acetate copolymer (60:40) viscosity 3.3–4 cps, M.W. 45,000–60,000: 0.25 g
Ethyl alcohol, sufficient for: 50°
Tartaric acid, sufficient for: pH 6
Water, sufficient for: 100 cc When applied to partially white blond hair, this hair setting lotion imparts thereto very pleasing lilac glints and a partially de-yellowing effect.

EXAMPLE 36

A hair dye composition is prepared by admixing the following components:
Polymer of Example 17: 0.375 g
Vinyl acetate crotonic acid copolymer (90:10) M.W. 45,000–50,000: 1.5 g Vinylpyrrolidone-vinyl acetate copolymer (60:40) viscosity 3.3–4 cps M.W. 45,000–60,000: 0.25 g
Ethyl alcohol, sufficient for: 50°
Tartaric acid, sufficient for: pH 6
Water, sufficient for: 100 cc When applied to naturally deep chestnut colored hair, this hair setting lotion imparts to the hair very beautiful mahogany glints.

EXAMPLE 37

A hair dye composition is prepared by admixing the following components:
4-N-γ-amino-propyl-amino-1-N'-methylamino anthraquinone: 0.145 g
Polymer of Example 16: 1.14 g
Polymer of Example 21: 1.464 g
Vinyl acetate crotonic acid copolymer (90:10) M.W. 45,000–50,000: 1.5 g
Vinylpyrrolidone-vinyl acetate copolymer (60:40) Viscosity 3.3–4 cps, M.W. 45,000–60,000: 0.25 g
Ethyl alcohol, sufficient for: 50°
Tartaric acid, sufficient for: pH 6
Water, sufficient for: 100 cc When applied to light chestnut colored hair, this solution gives the hair an extremely natural light chestnut shade.

EXAMPLE 38

A hair dye composition is prepared by admixing the following components:
Polymer of Example 14: 0.366 g
Vinyl acetate crotonic acid copolymer (90:10) M.W. 45,000–50,000: 1.5 g
Vinylpyrrolidone-vinyl acetate copolymer (60:40) viscosity 3.3–4 cps, M.W. 45,000–60,000: 0.25 g
Benzylidene camphor: 0.3 g
Ethyl alcohol, sufficient for: 50°
Tartaric acid, sufficient for: pH 6
Water, sufficient for: 100 cc When applied to grey hair which is 90% white, this hair setting lotion restores the proper sheen, with an especially luminous and esthetic looking iridescent color.

EXAMPLE 39

A hair dye composition is prepared by admixing the following components:
Aqueous solution (5%, pH 4.5) of the hydrochloride of the polymer of Example 20: 2.22 g
Polyvinylpyrrolidone, M.W.=40,000: 0.5 g
Trimethylcetylammonium bromide: 0.2 g
Quaternized polyvinylpyrrolidone, sold under the name "GAFQUAT 734" (active ingredients): 0.4 g
Ethyl alcohol, sufficient for: 12°
Tartaric acid, sufficient for: pH 5.5
Water, sufficient for: 100 cc This rinse is applied to light blond hair. After drying, the hair easily untangles and has a lovely light blond shade with a slightly pearly sheen.

EXAMPLE 40

A hair dye composition is prepared by admixing the following components:
Polymer of Example 15: 1.5 g
Vinylpyrrolidone-vinyl acetate copolymer (60:40) viscosity 3.3–4 cps, M.W. 45,000–60,000: 0.5 g
Trimethylcetylammonium bromide: 0.1 g
$H_2O_2$ (200 volumes), sufficient for: 10 vol.
Ethyl alcohol, sufficient for: 55°
Orthophosphoric acid, sufficient for: pH 3
Water, sufficient for: 100 cc When applied to natural light chestnut colored hair, this lotion, after drying, brightens the hair and gives it particularly warm and luminous copper glints.

EXAMPLE 41

A hair dye composition is prepared by admixing the following components:
Polymer of Example 14: 0.736 g
Hydroxyethylcellulose, sold under the name of "CELLOSIZE WP 3": 3.3 g
Citric acid, sufficient for: pH 6
Water, sufficient for: 100 g When applied for 20 minutes to hair which has previously been bleached light blond, this composition, after rinsing with water, shampooing and drying, gives the hair a beautiful ash-blond shade.

EXAMPLE 42

A hair dye composition is prepared by admixing the following components:
Polymer of Example 17: 2 g
"SIPOL SX" wax [mixture of fatty alcohols $C_{16}$–$C_{18}$ (90% by wt.) and sodium lauryl sulphate (10% by wt.)]: 2 g
"UKANIL 25" [fatty alcohol ($C_{13}$–$C_{15}$) oxyethylenated with 2.8 moles of ethylene oxide]: 3 g
"UKANIL 43" [fatty alcohol ($C_{13}$–$C_{15}$) oxyethylenated with 7 moles of ethylene oxide]: 2 g
Trimethylcetylammonium bromide: 1.5 g
Ethyl "Cellosolve": 10 cc
Citric acid, sufficient for: pH 8
Water, sufficient for: 100 g 90 grams of this mixture are incorporated into an aerosol container together with 10 g of a propellant mixture comprising 43 parts of 1,2-dichloro-1,1,2,2-tetrafluoro ethane and 57 parts of dichlorodifluoromethane. About 25 g of this foam are applied to blond hair and 10 minutes later, after rinsing in warm water and drying, the hair becomes consistently and discreetly colored mahogany blond.

EXAMPLE 43

A hair dye composition is prepared by admixing the following components:
Polymer of Example 7: 1.7 g
Polymer of Example 16: 0.26 g
Polymer of Example 17: 13.6 g
Alkylphenol polyethoxyether sold under the name "REMCOPAL 334": 22 g
Alkylphenol polyethoxyether sold under the name "REMCOPAL 349": 22 g
Propylene glycol: 14 g
Pentasodium salt of diethylenetriaminepentacetic acid sold under the name "MASQUOL DTPA": 2.5 g
Ammonia 22° Bé: 7 cc
Water, sufficient for: 100 g Just before use, 20 g of a $H_2O_2$ solution (6% by weight) are incorporated into 20 g of this gel. A jellified liquid is then obtained which is applied for 30 minutes to blond hair that has been somewhat sensitized by prior treatments. After rinsing in warm water and drying, the hair has a very luminous light mahogany coppery blond color.

EXAMPLE 44

A hair dye composition is prepared by admixing the following components:

Paratoluylene diamine: 0.15 g
Paraaminophenol: 0.35 g
2-methyl-5-N-β-hydroxyethylaminophenol: 0.45 g
Polymer of Example 15: 12 g
Alkylphenol polyethoxyether sold under the name "REMCOPAL 334": 22 g
Alkylphenol polyethoxyether sold under the name "REMCOPAL 349": 22 g
Butyl "Cellosolve": 8 g
Propylene glycol: 8 g
Ethylene-diamine-tetraacetic acid: 0.2 g
Hydroquinone: 0.2 g
Sodium acid sulphite, 36° Bé: 1 cc
Ammonia 22° Bé: 10 cc
Water, sufficient for: 100 cc Just before use, 20 g of this semi-transparent liquid are mixed with 20 g of a $H_2O_2$ solution (6% by weight) and the resulting gel is applied to very light blond hair which is 90% white. After rinsing with water, shampooing and drying, the hair is dyed a slightly iridescent coppery golden blond color.

What is claimed is:

1. A water-soluble polymer dye which is the reaction product of
   (1) as a water-soluble cationic polymer a polyamino amide, with
   (2) as a chromophore or chromogen group carrying compound, an aromatic amine, said aromatic amine being linked to said polyamino amide by a tertiary amine group,
the main chain of said polymer dye having at least 10% aliphatic amine groups relative to the total number of amine groups in said main chain.

2. A water-soluble polymer dye which is the reaction product of
   (1) as a water-soluble cationic polymer a polyamino amide, with
   (2) as a chromophore or chromogen group carrying compound, an aromatic amine having a chloroacetylated extranuclear amine group, said aromatic amine being linked to said polyamino amide by a tertiary amine group,
the main chain of said polymer dye having at least 10% aliphatic amine groups relative to the total number of amine groups in said main chain.

3. A water-soluble polymer dye which is the reaction product of
   (1) as a water-soluble cationic polymer a polyamino amide having recurring units of the formula
   $[NHCH_2CH_2NHCH_2CH_2NHCO(CH_2)_4CO]$ with
   (2) as a chromophore or chromogen group carrying compound, a compound of the formula said compound being linked to said polyamino amide by a tertiary amine group, and the main chain of said polymer dye having at least 10% aliphatic amine groups relative to the total number of amine groups in said main chain.

4. A water-soluble polymer dye for coloring keratinic fibers comprising
   (1) a water-soluble cationic polymer having recurring units of the formula $+NHCH_2CH_2NHCH_2CH_2NHCO(CH_2)_4CO+$ (2) a chromophore group carrying compound, said chromophore group carrying compound having the formula (3) an amine group which links (1) and (2) and the main chain of the polymer dye has at least 10% aliphatic amine groups relative to the total number of amine groups of said chain.

5. A process for producing a water-soluble polymer dye for coloring keratinic fibers comprising (1) a water-soluble cationic polymer, (2) a chromophore or chromogen group carrying compound, either of said chromophore or chromogen group carrying compound further containing aryl or arylaliphatic groups, (3) an amine group which links (1) and (2) and the main chain of the polymer has at least 10% aliphatic amine groups relative to the total number of amine groups of said chain whereby the absorption of the said polymer dye on said fibers is facilitated, the steps comprising reacting at least one reactive colored compound having one or more $-NHCOCH_2Cl$ radicals with at least one cationic resin having primary, secondary or tertiary alkylatable amine groups.

* * * * *